US005780230A

United States Patent [19]
Li et al.

[11] Patent Number: 5,780,230
[45] Date of Patent: Jul. 14, 1998

[54] COMPOSITIONS AND METHODS FOR HUMAN SPERM ACTIVATION AND QUANTITATIVE ASSESSMENT OF HUMAN SPERM GENOME REPLICATION

[75] Inventors: Honghua Li, Cherry Hill; Yong-Sheng Xu, Haddonfield, both of N.J.

[73] Assignee: Coriell Institute for Medical Research, Camden, N.J.

[21] Appl. No.: 540,327

[22] Filed: Oct. 6, 1995

[51] Int. Cl.$^6$ .............................. C12Q 1/68; C12N 1/06
[52] U.S. Cl. .......................... 435/6; 435/259; 435/317.1
[58] Field of Search ................................. 435/194, 91.1, 435/6, 259, 317.1

[56] References Cited

U.S. PATENT DOCUMENTS 5,358,847  10/1994  Brown ........................................ 435/6

OTHER PUBLICATIONS

R. Yanagimachi, "Zone–Free Hamster Eggs: Their Use in Assessing Fertilizing Capacity and Examining Chromosomes of Human Spermatozoa", Gamete Research 10:187–232 (1984).

M.J. Lohka and Y. Masui, "Formation in vitro of Sperm Pronuclei and Mitotic Chromosomes Induced by Amphibian Ooplasmic Components", Science 220:719–721 (1983).

R. M Harland and R.A. Laskey, "Regulated Replication of DNA Microinjected into Eggs of Xenopus laevis", Cell 21:761–771. (1980).

I.R. Kill et al., "The timing of the formation and usage of replicase clusters in S–phase nuclei of human diploid fibroblasts", J. Cell Science 100:869–876 (1991).

G.H. Leno and R. Munshi, "Initiation of DNA Replication in Nuclei from Quiescent Cells Requires Permeabilization of the Nuclear Membrane", J. Cell Biology 127:5–14 (1994).

D.B. Brown et al., "Chromatin Decondensation and DNA Synthesis in Human Sperm Activated In Vitro by Using Xenopus laevis Egg Extracts", J. Experimental Zoology 242:215–231 (1987).

K. Ohsumi et al., "Human Sperm Nuclei Can Transform Into Condensed Chromosomes in Xenopus Egg Extracts", Gamete Research 20:1–9 (1988).

M. Montag et al., "In Vitro Decondensation of Mammalian Spermand Subsequent Formation of Pronuclei–Like Structures for Micromanipulation", Molecular Reproduction and Development 33:338–346 (1992).

D.B. Brown and M.N. Nagamani, "Use of Xenopus laevis Frog Egg Extract in Diagnosing Human Male Unexplained Infertility", Yale J. of Biology and Medicine 65:29–38 (1992).

J. F. Griveau et al., "Decondensation of Human Sperm Nuclei and HP1 Protamine Degradation from Normospermia and Asthenospermia in Xenopus Egg Extracts", Archives of Andrology 29:127–136 (1992).

D.B. Brown et al., "Some cases of human male infertility are explained by abnormal in vitro human sperm activation", Fertility and Sterility 64:612–622 (1995).

H. Li et al., "Amplification and analysis of DNA sequences in single human sperm and diploid cells", Nature 355:414–417 (1988).

R. Saiki et al., "Enzymatic Amplifiction of β–Globin Genomic Sequences and Restriction Site Analysis for Diagnosis of Sickle Cell Anemia", Science 230:1350–1354 (1985).

K.B. Mullis and F.A. Faloona, "Specific Synthesis of DNA in Vitro via a Polymerase–Catalyzed Chain Reaction", Methods in Enzymology 155:335–351 (1987).

X.F. Cui et al., "Single–sperm typing: Determination of genetic distance between the $^G$γ–globin and parathyroid hormone loci by using the polymerase chain reaction and allele–specific oligomers", Proceedings of the National Academy of Science USA 89:9389–9393 (1989).

N. Arnheim et al., "PCR Analysis of DNA Sequences in Single Cells: Single Sperm Gene Mapping and Genetic Disease Diagnosis", Genomics 8:415–419 (1990).

A. Chakravarti, "The Behavior of Meiosis in Sperm", American J. Human Genetics 55:421–422 (1994).

L. Zhang et al., "Whole genome amplification from a single cell: Implications for genetic analysis", Proceedings of the National Academy of Science USA 89:5847–5851 (1992).

J. Newport, "Nuclear Reconstitution in Vitro: Stages of Assembly around Protein–Free DNA", Cell 48:205–217 (1987).

J.J. Blow and R.A. Laskey, "Initiation of DNA Replication in Nuclei and Purfied DNA by a Cell–Fee Extract of Xenopus Eggs", Cell 47:577–587 (1986).

J.J. Blow and P. Nurse, "A cdc2–like Protein Is Involved in the Initiation of DNA Replication in Xenopus Egg Extracts", Cell 62:855–862 (1990).

A.W. Murray, "Cell Cycle Extracts", Methods in Cell Biology 36:581–605 (1991).

J.J. Blow and J.V. Watson, "Nuclei act as independent and integrated units of replication in a Xenopus cell–free DNA replication system", The EMBO J. 6:1997–2002 (1987).

C. Smythe and J.W. Newport, "Systems for the Study of Nuclear Assembly, DNA Replication, and Nuclear Breakdown in *Xenopus laevis* Egg Extracts", Methods in Cell Biology 35:449–467 (1991).

*Primary Examiner*—James Ketter
*Attorney, Agent, or Firm*—John S. Child, Jr.; Dann, Dorfman, Herrell and Skillman

[57] ABSTRACT

A composition is provided, which comprises a purified cytoplasmic extract from eggs of *Xenopus laevis* which is capable of supporting activation of human sperm and complete replication of a human sperm genome. Methods of using the extract to achieve complete replication of the sperm genome are disclosed. A flow cytometric method for quantitatively monitoring replication of human sperm genomes is also disclosed. This method can be used for clinical assessment of sperm quality in a test sample of human sperm from an infertile male donor.

21 Claims, 4 Drawing Sheets

COMPOSITIONS AND METHODS FOR HUMAN SPERM ACTIVATION AND QUANTITATIVE ASSESSMENT OF HUMAN SPERM GENOME REPLICATION

FIELD OF THE INVENTION

This invention relates to the field of fertility and genetic analysis of human sperm. In particular, the present invention provides compositions and protocols for complete replication of the human sperm genome, utilizing an improved method for preparing fresh and frozen *Xenopus laevis* egg extracts used to perform the protocol. The invention also provides methods for quantitatively assessing the quality and DNA replication of human sperm and for performing genetic analysis of the human male genome.

BACKGROUND OF THE INVENTION

Measurement of the ability of human sperm to completely replicate its DNA is important for the healthcare goals of predicting male fertility, determining causes of idiopathic infertility and performing genetic analysis of the male genome. During the seventy-four day spermatogenesis period in humans, variations in a number of factors can cause changes in sperm quality. Although male infertility can be diagnosed by assays of sperm counts, morphology, and motility, only two assays can be used for cytologically and biochemically analyzing the sperm quality.

One well-known fertility assay is the sperm penetration assay (SPA)(R. Yanagimachi, *Gamete Res.* 10:187–232 (1984)). In the SPA, the ability of human sperm to penetrate zona-free Chinese hamster eggs is measured. Chinese hamster zona-free eggs permit entry of sperm from a wide variety of other species, provided that the sperm have completed preliminary capacitation and the acrosome reaction essential to normal fertilization of all mammalian species. Thus the SPA measures the sperm's ability to perform the preliminary steps of fertilization based on the percentage of zona-free Chinese hamster eggs which are penetrated by an individual's sperm. Although this assay allows some biochemical analysis, many details, such as the percentage of sperm which are decondensed and the extent of DNA replication, are not addressed. Other drawbacks to the SPA method include the small number of eggs (40 to 50) produced by each female hamster and the requirement of an animal facility for housing the hamsters. Due to the drawbacks of the SPA, more efficient protocols and assays for diagnosing male infertility have been sought.

Another well-known protocol uses egg extracts from the African toad, *Xenopus laevis*, for the activation of sperm. The use of toad eggs from one species to activate toad sperm from another species was first reported using *Rana pipiens* egg extracts to activate *Xenopus laevis* demembranated sperm (M. J. Lohka and Y. Masui, *Science* 220:719–721 (1983)). It was shown subsequently that Xenopus egg extracts can be used to support at least some level of replication of various DNA from other species ranging from viral and bacteriophage DNA (R. M. Harland and R. A. Laskey, *Cell* 21:761–771 (1980)) to human DNA from somatic cells (I. R. Kill et al., *J. Cell Sci.* 100:869–876 (1991); G. H. Leno and R. Munshi, *J. Cell Bio.* 127:5–14 (1992)). Since then, several protocols using Xenopus egg extracts for human sperm activation and male infertility diagnosis have been reported (D. B. Brown et al., *J. Exp. Zool.* 242:215–231 (1987); K. Ohsumi et al., *Gamete Res.* 20:1–9 (1988); M. Montag et al., *Mol. Reprod. Dev.* 33:338–346 (1992); D. B. Brown and M. N. Nagamani, *Yale J. Biol. Med.* 65:29–38 (1992); J. F. Griveau et al., *Arch. Androl.* 29:127–136 (1992)).

Brown et al. developed an in vitro human sperm activation system using Xenopus egg extracts to study the events of nuclear swelling-chromatin decondensation and DNA synthesis that occur in vivo following fertilization (D. B. Brown et al., *J. Exp. Zool.* 242:215–231 (1987)). In this system, lysolecithin-permeabilized human sperm were incubated in an extract prepared from *Xenopus laevis* eggs. Eggs were collected from Xenopus toads which had been primed with two injections of human chorionic gonadotropin in the morning and evening preceding collection. Before preparing the extract, some of the eggs were activated by an electric shock of 80 V for 200 milliseconds. The eggs were dejellied in cysteine, then lysed and fractionated by centrifugation. A second centrifugation step was used to further purify the egg extract.

Permeabilized human sperm from fertile donors were then incubated with the Xenopus egg extract prepared as described above and the sperm nuclei were monitored microscopically and by autoradiography to observe chromatin decondensation-nuclear swelling and DNA synthesis respectively. Using phase contrast microscopy and Giemsa-stained autoradiographs, Brown et al. observed morphological changes in the sperm nuclei after incubation including nuclear swelling and a chromatin decondensation-recondensation cycle. Brown et al. also observed incorporation of $^3$H-thymidine into the sperm nuclei which indicated that DNA synthesis had initiated in the sperm nuclei after incubation with the egg extract. After 55 minutes of incubation, all the sperm nuclei had incorporated the $^3$H-thymidine label; however, the amount of replication was not determined.

Brown et al. studied the effects of Xenopus egg activation by electric shock and freezing and thawing the egg extract on chromatin decondensation-nuclear swelling and DNA synthesis. They reported that activating the eggs did not enhance sperm chromatin decondensation-nuclear swelling or DNA synthesis. Brown et al. thus concluded that Xenopus eggs required no activation to induce the fertilization-related events of decondensation, pronuclei formation, nuclear envelope breakdown and recondensation in incubated sperm. When the Xenopus egg extract was frozen and then thawed, Brown et al. observed that the sperm incubated in the freeze-thawed extract underwent chromatin decondensation-nuclear swelling. They did not, however, observe DNA synthesis in sperm incubated with the freeze-thawed egg extract and concluded that freezing and thawing the egg extract blocked DNA synthesis in the sperm.

In later studies, Brown and co-workers used the *Xenopus laevis* egg extract to investigate unexplained human male infertility in an assay called the human sperm activation assay (HSAA)(D. B. Brown and M. Nagamani, *Yale J. Biol. Med.* 65:29–38 (1992); D. B. Brown et al., *Fertility and Sterility* 64:612–622 (1995)). The Xenopus egg extract was prepared as in the previous study with the exception that the Xenopus eggs were not activated and the effect of freezing and thawing the egg extract was not examined. Furthermore, in the later study, eggs that were in the process of being readsorbed by the toads were removed before the extract was prepared. The fertile and infertile sperm were incubated with the egg extract and chromatin decondensation, DNA synthesis and chromatin recondensation were evaluated using phase contrast microscopy and autoradiography as in the previous report. The fertile sperm exhibited normal chromatin decondensation and DNA synthesis; however, some of the infertile sperm exhibited a slow rate of chromatin decondensation and a low level of DNA synthesis. These studies indicated that infertile sperm may produce abnormal results in the human sperm activation assay despite normal results in other fertility assays such as sperm count, motility and morphology.

Montag et al. studied the process of nuclear reformation of pre-decondensed human sperm genomes upon incubation with Xenopus laevis egg extract (M. Montag et al., Mol. Reprod. Dev. 33:338–346 (1992)). Similar to the Brown et al. procedure for preparing Xenopus egg extract, Montag et al. injected the Xenopus toads with two doses of human chorionic gonadotropin at an interval of five hours starting approximately 21 hours prior to collection of the eggs. The eggs were dejellied in cysteine and electroactivated with 12 V alternating current for 1 second. After crushing by centrifugation, the extract fraction was removed and recentrifuged. The clear soluble supernatant, comprising the purified egg extract, was removed and immediately frozen in liquid nitrogen. The membrane vesicle fraction was diluted with egg extract buffer and concentrated by recentrifugation through a sucrose cushion.

The egg extract was thawed and supplemented with an ATP regenerating system containing ATP, phosphocreatine and phosphokinase. The solution was added to the pre-decondensed sperm and incubated before adding the purified membrane fraction from the egg extract preparation. Bromodeoxyuridine (BrdU) incorporation was used to monitor DNA replication in this system. Incorporation was detected with anti-BrdU antibodies conjugated to fluorescein isothiocyanate (FITC), followed by microscopic examination. Montag et al. observed that when incubated in Xenopus egg extract, the pre-decondensed human sperm nuclei formed pronuclei-like structures. The incorporation of BrdU indicated that DNA synthesis had initiated and Montag et al. concluded that the removed sperm nuclei were viable. However, because Montag et al. used pre-decondensed sperm, it is unclear from that report whether the Xenopus egg extract could support full genome replication.

The possibility of using Xenopus egg extracts for human sperm genome replication was shown by Brown et al. and Montag et al. Although some DNA synthesis in human sperm nuclei was qualitatively demonstrated by tritiated thymidine or bromodeoxyuridine incorporation in these studies, the extent of DNA replication was not clear because these protocols were limited to qualitative microscopic or, at best, semi-quantitative microscopic analyses. The Brown et al. and Montag et al. assays do not provide a means for quantitatively measuring whether complete DNA replication has occurred in the sperm nuclei. It is necessary to analyze a large number of sperm from each donor to obtain the highly reliable results required for clinical diagnosis. These assays cannot be used to monitor DNA replication in a given sperm population accurately because only very few sperm cells can be analyzed. These protocols also do not use animal treatment methods and egg extract preparations which are effective for inducing the sperm nuclei to undergo complete replication of its genome.

Complete in vitro genome replication of the sperm from higher organisms such as humans, livestock, and fruit trees could have profound biomedical and economic impact by improving genetic research. Generally, genetic linkage studies through inbreeding or through family analysis in humans are either difficult or impractical because reproductive cycles are very long and the reproductive coefficient for most mammals, i.e., the number of offspring from each female during her life, is very small. Li et al. described an alternative approach in which individual gametes are used as subjects for genetic analysis instead of studying parents and their offspring (H. Li et al., Nature 335:414–417 (1988)). Haploid gametes like sperm are ideal for genetic analysis because these cells are meiotic products and are genetically informative.

The advantages for using gametes include the availability of a huge number of gametes that can be easily obtained for genetic analysis from each male organism without waiting for their offspring to develop and grow. In addition, with haploid cells, the complications associated with the "mixed" genetic information from both parents in the diploid cells are avoided.

Individual sperm cells have been genotyped by amplifying the polymorphic DNA sequences at genetically polymorphic loci to analyzable amounts using the polymerase chain reaction (PCR, R. Saiki et al., Science 230:1350–1354 (1985); K. B. Mullis and F. A. Faloona, Meth. Enz. 155:335–351 (1987)) and then determining the genotype at these loci through analysis of the PCR product. The ability to type individual gametes has eliminated the limitations, such as sample size and long reproductive cycles, which are inherently associated with the traditional inbreeding or family approaches.

Cui et al. applied this approach in determining the genetic distance between two gene loci on chromosome 11 (X. F. Cui et al., Proc. Natl. Acad. Sci. USA 89:9389–9393 (1989)). Since then a number of genetic studies using this approach have been performed (as reviewed by N. Arnhiem et al., Genomics 8:415–419 (1990) and A. Chakavarti, Am. J. Hum. Genetics 55:421–422 (1994)). However, the application of single cell typing is restricted by several limitations. First, since there is only a single copy of the target sequences in haploid cells, the samples cannot be reused and the experiment cannot be repeated. Second, target sequences in a small fraction of samples may not be amplified to an analyzable amount, which in turn affects the detection of low-frequency genetic recombinations. The second limitation has been removed to a large extent by the development of the in vitro whole genome amplification approach using the Taq DNA polymerase (L. Zhang et al., Proc. Natl. Acad. Sci. USA 89:5847–5851 (1992)). However, both limitations could be avoided by completing multiple rounds of haploid genome replication with high accuracy using an in vivo or hemi-in vivo system.

Xenopus laevis egg extract could provide an ideal system for accomplishing one or more complete rounds of haploid genome replication. Unlike many organisms in which very few eggs can be obtained from each mature female individual, a large number of eggs with a complete set of factors supporting sperm activation and DNA replication can be collected from a mature female Xenopus laevis toad. Furthermore, the egg extract from each Xenopus laevis egg can be used for replicating approximately 3000 sperm genomes, as estimated from studies using lambda phage DNA (J. Newport, Cell 48:205–217 (1987)).

However, the complete replication of the human sperm genome in Xenopus laevis egg extracts has not been demonstrated. Moreover, there are conflicts in the published literature as to which steps in the preparation of Xenopus egg extracts are important to accomplish complete or multiple rounds of genome replication. Thus, it is clear that the fields of infertility assessment and haploid genotyping would benefit from a demonstrably effective method for preparing high quality Xenopus egg extracts capable of supporting sperm activation and complete genome replication in vitro. It would be of particular benefit if the egg extract were capable of supporting sperm genome replication even after freezing and thawing the extract. It would be of further benefit to provide a protocol for complete or multiple replication of the human sperm genome, which incorporates a method for quantitatively measuring or monitoring replication to determine when replication is complete. Such methods and compositions are presently unavailable.

SUMMARY OF THE INVENTION

The present invention provides compositions and methods for achieving complete replication of the human sperm genome, utilizing an improved method for preparing cytoplasmic extracts from eggs of *Xenopus laevis*. The invention also provides methods for quantitatively assessing sperm quality and DNA replication of human sperm.

According to one aspect of the invention, a composition comprising a purified cytoplasmic extract from eggs of *Xenopus laevis* is provided, which is capable of supporting activation of human sperm and complete replication of a human sperm genome. The composition is prepared by a multi-step method comprising certain steps which, singly or combined, contribute to the high quality of the egg extract produced thereby. In the method, a sexually mature female *Xenopus laevis* toad is primed for egg production by administering a gonadotropin hormone in an amount effective to stimulate egg production. The priming comprises a first priming step in which a first aliquot of gonadotropin is administered more than one day (preferably 2-3 days) prior to egg collection. A second priming step follows, wherein at least one additional aliquot of gonadotropin is administered between about 12 and about 24 hours prior to egg collection. After the toad has laid eggs, those eggs are collected and combined with unlaid eggs expressed from the toad by squeezing. The eggs are de-jellied and washed, after which the eggs are sorted by removing substantially all eggs which appear damaged or of non-uniform character as compared with normal, intact eggs from *Xenopus laevis*. The eggs are then activated to shift them from mitotic phase to S phase, and the eggs are rinsed with a compatible rinsing solution. The eggs are then packed (i.e., concentrated) by removing substantially all excess rinsing solution from the rinsed eggs. In a preferred embodiment, this is accomplished by a low-speed centrifugation, which provides the additional benefit of enabling further removal of damaged or non-uniform eggs, inasmuch as these eggs form a layer on the surface of the packed egg mass after centrifugation. The cytoplasmic extract is prepared from the packed eggs by a two-step centrifugation process. First, an initial cytoplasmic fraction is prepared by subjecting the eggs to centrifugation under conditions resulting in crushing of the eggs and separation of the initial cytoplasmic fraction from other egg components, followed by a procedure for collecting only the initial cytoplasmic fraction. The initial cytoplasmic fraction is then subjected to second centrifugation under conditions resulting in separation of the cytoplasmic extract from contaminants, such as vesicular components, remaining in the initial cytoplasmic fraction. The purified cytoplasmic extract is carefully removed away from these contaminants. The purified cytoplasmic extract prepared by the aforementioned method is of extremely high quality, and is found to be active even after freezing and thawing.

In a preferred embodiment of the present invention, the above-described egg extract is prepared by a method in which the first priming step comprises administering pregnant mare gonadotropin and the second priming step comprises administering human chorionic gonadotropin. In another preferred embodiment, the egg extract is prepared by a method in which the egg sorting step comprises manual removal of physically damaged eggs and eggs of non-uniform size, shape and color, and may further comprise a low-speed centrifugation followed by skimming of damaged or non-uniform eggs from the top of the packed egg surface formed after the centrifugation. In another preferred embodiment of the invention, the egg extract is prepared by a method in which egg activation is accomplished by exposing the eggs to an amount of calcium ionophore effective to induce the shift from mitotic phase to S phase.

The above-described methods for producing the Xenopus egg extract of the invention embodies several improvements to currently available methods for producing Xenopus egg extracts. Specifically, these are: (1) including, between the rinsing of the de-jellied eggs and the preparing of the initial cytoplasmic fraction, the step of concentrating the rinsed eggs by removing substantially all of the rinsing solution from rinsed eggs; (2) including in the priming of the toad for egg production the step of administering an additional aliquot of the gonadotropin more than one day prior to egg collection; (3) removing from the de-jellied eggs substantially all eggs which appear damaged or of non-uniform character as compared with normal, intact eggs from *Xenopus laevis*; and (4) activating the eggs to shift from mitotic phase to S phase in their cell cycle.

According to another aspect of the present invention, a method for completely replicating human sperm genomes is provided, which utilizes the purified cytoplasmic extract of *Xenopus laevis* eggs prepared as described hereinabove. A sample of demembranated, dithiothrietol-treated human sperm is combined with the above-described Xenopus egg extract, in the presence of nucleotide triphosphatase for DNA synthesis and reagents for regenerating ATP. This combination of ingredients produces a replication reaction mixture wherein replication of genomes disposed within the human sperm begins to occur. The replication reaction is continued for a time period sufficient to enable the complete replication of the human sperm genomes in the reaction mixture.

According to another aspect of the present invention, the above-described replication reaction is quantitatively monitored at selected intervals during the time period in which replication is occurring. To accomplish this, an aliquot of the replication mixture is removed at one or more selected intervals during the time period of replication, and the replication in that aliquot is terminated. The sperm pronuclei in the aliquot are then uniformly labelled with a quantitatable DNA-specific detectable reporter substance, and the quantity of the detectable reporter substance in the aliquot is then measured. This quantity is directly proportional to the amount of DNA present in the sperm pronuclei in that aliquot. In preferred embodiments of the invention, the quantitative detection and measurement is performed by flow cytometry.

According to another aspect of the invention, the aforementioned replication methods may be adapted for quantitative assessment of DNA replication in a test sample of human sperm from a suspected infertile donor. In the adaptation, a purified xenopus egg extract as described above is utilized, which is supplemented with nucleotide triphosphatase for DNA synthesis and reagents for regenerating ATP. This "replication solution" is combined with either a test sample of demembranated, dithiothrietol-treated sperm from the suspected infertile donor or a control sample of similarly prepared sperm from a known fertile donor. The replication reactions comprising either the test sperm sample or the control sperm sample are continued for a predetermined time period. At selected intervals during that period, equivalent aliquots of each of the control and test replication reaction is removed and the replications are terminated in each aliquot. The sperm pronuclei in each aliquot are then uniformly labelled with a quantitatable DNA-specific detectable reporter substance, and that quantity is measured. The quantity of detectable reporter reflects the amount of DNA in each nucleus present in the test replication reaction or the control replication reaction at the selected time interval. By comparing the amount of DNA present in the test reaction versus the control reaction, a determination can be made as to the adequacy of DNA replication of sperm in the test sample.

The compositions and methods of the invention, as described hereinabove and in greater detail below, can be used to advantage in a variety of practical applications. The following detailed description and examples set forth preferred embodiments for making and using the compositions of the invention, and for practicing the methods of the invention.

BRIEF DESCRIPTION OF THE DRAWINGS

FIGS. 1A–1P: Histograms generated from flow cytometric analysis of sperm DNA replication in *Xenopus laevis* egg extracts. Unless otherwise indicated, egg extracts were from a single toad, and were stored in liquid nitrogen for two weeks prior to use. Unless otherwise indicated, human sperm were treated with lysolecithin and dithiothreitol prior to use. The x-axis represents arbitrary fluorescence intensity, which is proportional to the amount of DNA present in each scanned sperm. The y-axis represents the number of events recorded during the scanning session (i.e., the number of sperm analyzed in the session). Experiments shown in FIG. 1A through FIG. 1P are as follows:

1A In vitro decondensed *Xenopus laevis* sperm (control).

1B Demembranated *Xenopus laevis* sperm incubated for 4 hours with *Xenopus laevis* egg extract (control).

1C Human sperm incubated with *Xenopus laevis* egg extract.

1D In vitro decondensed human sperm (control).

1E Human sperm incubated for 1 hour with *Xenopus laevis* egg extract.

1F Human sperm incubated for 2 hours with *Xenopus laevis* egg extract.

1G Human sperm incubated for 4 hours with *Xenopus laevis* egg extract.

1H Human sperm incubated for 6 hours with *Xenopus laevis* egg extract.

1I Human sperm incubated for 9 hours with *Xenopus laevis* egg extract.

1J Human cell line GM 7038c incubated with *Xenopus laevis* egg extract.

1K Human sperm incubated for 2 hours with *Xenopus laevis* egg extract prepared from a second toad.

1L Human sperm incubated for 4 hours with *Xenopus laevis* egg extract prepared from the second toad.

1M Human sperm incubated for 3 hours with activated *Xenopus laevis* egg extract.

1N Human sperm incubated for 3 hours with non-activated *Xenopus laevis* egg extract.

1O *Xenopus laevis* sperm incubated for 5 hours with *Xenopus laevis* egg extract that had been stored in liquid nitrogen for 1.5 months.

1P Human sperm incubated for 5 hours with *Xenopus laevis* egg extract that had been stored in liquid nitrogen for 1.5 months.

DETAILED DESCRIPTION OF THE INVENTION

The present invention provides an improved *Xenopus laevis* egg extract which, in preferred embodiments, is prepared by the following general method:

a. The xenopus laevis toads are primed with a gonadotropin, (preferably pregnant mare serum gonadotropin) preferably two to three days prior to egg collection. The toads are primed again, preferably with human chorionic gonadotropin, 12 to 24 hours prior to egg collection.

b. The Xenopus eggs are collected and dejellied using cysteine. After dejellying, the eggs are sorted to remove low quality or abnormal eggs, as described in greater detail below.

c. The Xenopus eggs are activated to shift from mitotic to S phase, preferably using the calcium ionophore A23187.

d. The xenopus eggs are rinsed and packed, preferably using centrifugation to remove as much excess washing buffer as possible and also to separate the high quality eggs from the low quality eggs which separate into an upper layer during centrifugation.

d. A low-speed supernatant of Xenopus egg cytoplasm (sometimes referred to herein as the "initial cytoplasmic fraction") is prepared by centrifuging to separate the egg components into three fractions, removing the middle layer of cytoplasm. The middle layer is recentrifuged to further separate the golden cytoplasmic fraction from the yellow vesicular fraction. This cytoplasmic fraction is sometimes referred to herein as the "purified cytoplasmic extract", "the cytoplasmic extract", or "the egg extract".

e. The egg extract is then optionally frozen and stored, preferably in liquid nitrogen.

It has been discovered in accordance with the present invention that certain of the steps set forth above, which differ from currently available methods, are important or critical for the production of high quality *Xenopus laevis* egg extract that can be used fresh or previously frozen to support robust human sperm activation and complete human sperm genome replication in vitro. For example, the method of the invention incorporates a pre-priming or early priming step 2 or 3 days prior to egg collection, which is believed to increase egg production and to stimulate production of high quality eggs. This early priming step (preferably using pregnant mare serum gonadotropin) is not used in currently available methods, which limit priming to within one day of egg collection.

The method of the invention also employs egg sorting to remove low quality or abnormal eggs. Egg sorting has been found to improve the quality of the Xenopus egg extract by removing eggs that are exceptionally big, eggs with necrotic changes and eggs that are discolored, lysed or misshaped. Although some egg sorting has been used in previous protocols, the present method employs more rigorous sorting criteria.

The method of the invention further employs egg activation which induces the eggs to complete mitosis and enter interphase. More functional egg extracts are obtained using activated eggs and egg activation has been found to improve replication efficiency and promote faster replication of human sperm DNA. Although egg activation has been experimented with in previous protocols, its importance to human sperm DNA replication has not been recognized.

The method of the invention still further employs egg packing to concentrate the egg extract after the washing step.

Egg packing by centrifugation also serves as a supplemental egg sorting step by separating the low quality eggs into the upper layer during centrifugation, which can thereafter be skimmed from the surface of the packed eggs. In addition, egg packing may improve freezing of Xenopus egg extract by removing excess aqueous solution which may interfere with freezing due to crystal formation or increased freezing time. This step is not present in currently available methods.

Finally, the method of the invention optionally employs freezing the Xenopus egg extract, preferably in liquid nitrogen. The frozen egg extract can be stored for up to 1.5 months before use in the replication of human sperm DNA. Frozen egg extract enables commercial production and shipping of the Xenopus egg extract to clinical laboratories where the extract can be used to perform human sperm DNA replication in fertility assays and other protocols.

Also in accordance with the present invention, quantitative methods have been developed to monitor the replication of populations of human sperm DNA in the *Xenopus laevis* egg extract described above.

a. Human Sperm Preparation: Human sperm are prepared by incubating the semen sample at 37° C., filtering the semen through a 15 μm mesh and pelleting the sperm by centrifugation. Sperm clumping has been a special problem for sperm purification. Usually, sperm are very "sticky" and they tend to clump together even at low centrifugation speeds. Clumping may be due to cell debris in the semen which causes the sperm to stick together. This problem can be overcome by filtering through a 15 μm mesh before centrifuging the sperm. The sperm are then demembranated using lysolecithin, and optionally frozen at −80° C.

b. Replication Reaction: In the replication reaction, the Xenopus egg extract prepared as described above are mixed with sperm prepared as described above and treated with DTT. The replication reaction is supplemented with an ATP energy regeneration system and nucleotide triphosphates for DNA synthesis. Replication reactions are incubated under appropriate conditions for a sufficient time to complete replication of the sperm genomes.

c. Flow Cytometry Analysis: The human sperm-egg extract replication reaction is stopped by diluting with buffer, preferably with sucrose to help prevent clumping. The pronuclei are then stained by incubation with a suitable nuclear stain, such as propidium iodide, in the presence of RNase. Flow cytometry is performed, for example, on a FACScan flow cytometer. The data are gated to exclude debris and a gated histogram which quantitatively shows the amounts of fluorescence for the single nuclei stained with fluorescent dye is generated. Flow cytometry is used to quantitatively assess DNA replication in a large population of sperm cells, thereby providing a more accurate assessment of sperm quality from a test sample of human semen. Moreover, this method is easily adaptable to accommodate a large number of human semen samples. Methods presently available in the art do not employ quantitative assessment of human sperm genome replication, and therefore are of lesser utility in large scale clinical assays.

d. Bromodeoxyuridine (BrdU) Incorporation Analysis: BrdU incorporation is an optional step used to qualitatively analyze human sperm DNA replication; it can be used to corroborate the quantitative flow cytometric analysis. An aliquot from the human sperm-egg extract replication reaction is incubated with BrdU and transferred to a poly-L-lysine-coated glass slide. The slide is incubated with antibodies to BrdU which are tagged with FITC, the slide is stained with propidium iodide and mounted with an anti-fading mounting solution. BrdU incorporation into the replicating DNA is measured using immunofluorescence.

Also in accordance with the present invention, specific applications of the general methods of the invention are provided. These applications include the use of high quality egg extract and quantitative replication in infertility assays and the use of complete replication or multiple sperm genome replications for haploid genotyping.

The detailed description set forth below sets forth preferred embodiments for practicing the present invention. To the extent that a particular composition or method is specified, it is for the purpose of illustration and is not intended to limit the invention.

1. Preparation of High Quality *Xenopus laevis* Egg Extract a. Priming the toads: The pre-priming step is important for increasing egg production and stimulating production of high quality eggs. In a preferred embodiment, pregnant mare serum gonadotropin is used for the first injection which occurs earlier than one day prior to egg collection. More preferably, the pregnant mare serum gonadotropin injection would occur 2 to 3 days prior to egg collection and most preferably, the pregnant mare serum gonadotropin injection would occur 3 days prior to egg collection. Other gonadotropins could also be used, as would be appreciated by those skilled in the art. These include, but are not limited to mammalian gonadotropins, such as pituitary gonadotropins, placental gonadotropins and chorionic gonadotropins.

b. Dejellying and sorting the eggs: The dejellying step is practiced according to standard methods, such as those set forth in Example 1. The sorting step is important for improving the quality of the Xenopus egg extract by removing eggs that are exceptionally big, eggs with necrotic changes and eggs that are discolored, lysed or misshaped. In a preferred embodiment, this is accomplished by manually removing the low quality eggs. However, other methods can be used, including, but not limited to removing the top layer of eggs after a low-speed centrifugation.

c. Egg activation: The egg activation step induces a transition from mitosis to S-phase in the eggs. It is important for preparing fully functional egg extracts, improving replication efficiency and for promoting faster replication of human sperm DNA. In a preferred embodiment, this is accomplished by treatment with a calcium ionophore, such as A23187. However, other methods can be used, including, but not limited to, activation by electric shock.

d. Egg packing: The egg packing step is important for preparing a more concentrated egg extract and for removing excess washing buffer which could interfere with efficient freezing of the prepared egg extract. In a preferred embodiment, this is accomplished by low-speed centrifugation. However, other methods can be used, including, but not limited to filtration of the eggs after washing. Egg packing by low speed centrifugation also provides an opportunity for further egg sorting, as described above.

e. Preparation of cytoplasmic extracts: The centrifugation and recentrifugation steps, which are used to lyse the eggs, isolate the cytoplasmic fraction and further purify the extract, are practiced according to standard methods, such as those set forth in Example 1.

f. Freezing egg extract: Freezing of the egg extract is important for extended storage of the extract, which allows commercial production and shipping of the Xenopus egg extract to clinical laboratories where the extract would be used to perform human sperm DNA replication in fertility assays. In a preferred embodiment, this is accomplished by freezing in liquid nitrogen, as described in greater detail in Example 1. However, other methods can be used, including, but not limited to, freezing the egg extract in liquid nitrogen and storing the frozen egg extract in dry ice. It should be noted that the quality of the extract may diminish more rapidly if stored in dry ice instead of liquid nitrogen.

2. Human Sperm Activation and Quantitative DNA Replication Assays a. Human sperm preparation: The human sperm preparation step is practiced according to methods which include a filtering step because sperm clumping has been a special problem for sperm purification. Usually, sperm are very "sticky" and they tend to clump together even at low centrifugation speeds. Clumping may be due to cell debris in the semen which causes the sperm to stick together. This problem can be overcome by filtering through a 15 µm mesh before centrifuging the sperm as set forth in Example 2.

b. Replication reaction: The replication reaction step is practiced according to standard methods, such as those set forth in Example 2. In vitro decondensation of the human sperm nuclei is used as a control to corroborate the flow cytometric results.

c. Bromodeoxyuridine incorporation analysis: The bromodeoxyuridine incorporation step is optional and is used to qualitatively corroborate flow cytometric results. This step was practiced according to standard methods, such as those set forth in Example 2.

d. Flow cytometry analysis: The flow cytometric step is important for quantitatively analyzing human sperm DNA replication in sperm activated by Xenopus egg extract. In a preferred embodiment, this is accomplished by treatment with propidium iodide and measurement of the corresponding fluorescence at selected time intervals during the replication reaction, as described in greater detail in Example 2. Of course, other fluorescent nuclear stains known in the art can be used (e.g., Hoeschst 33342).

3. Specific Applications a. Assessment of sperm quality:

Although several tests are presently available for diagnosing male infertility, none of these procedures can be used for examining the activation of the sperm nucleus and quantitatively measuring DNA replication after fertilization. With the method of the present invention, both decondensation and the precise extent of DNA replication can be analyzed in the human sperm populations of males with unexplained infertility.

b. Sperm genotyping:

Complete replication of the human sperm genome with the Xenopus egg extract will allow significant improvement in resolving short genetic distances and make it is possible to use this approach for locating genetic recombination hot spots. This success has also paved the way for establishing an in vivo system for multiplex rounds of replication of the haploid sperm genome. The compositions and methods of the invention can be used to provide a greater abundance of material from individual haploid genomes for genetic analysis. Furthermore, the replicated genome could be injected into enucleated cells including mammalian eggs or tissue culture cells to obtain more DNA for genetic analysis. As described in the Background section hereinabove, haploid gametes are ideal for genetic analysis, but their use is limited by the low abundance of target material available for analysis. The in vitro replication methods of the invention will alleviate this limitation.

EXAMPLES

Example 1

Preparation of High quality *Xenopus laevis* Egg Extracts

Materials and Methods

Sexually mature *Xenopus laevis* toads were ordered from Nasco and the active and healthy toads were chosen for egg production. If toads listed under Nasco catalog #LM351M are ordered, the toads should be ordered two months in advance. If toads listed under Nasco catalog #LM535M are ordered, the toads should be ordered two weeks in advance. The female *Xenopus laevis* toads were primed by injection of 50 IU pregnant mare serum gonadotrophin (Sigma) into the dorsal lymph sac using a syringe with 27 gauge needle (½ inch long) 3 days prior to egg collection. the toads were re-injected with 500–800 IU (depending on the size of the toads) of human chorionic gonadotrophin (hCG. CG-10. Sigma) 12 to 15 hours before egg collection. After the second injection, the toads were kept overnight in 3 liters of High Salt Barth solution (110 mM NaCl, 2 mM KCl, 1 mM $MgSO_4$, 0.5 mM $Na_2HPO_4$, 2 mM $NaHCO_3$, and 15 mM Tris-HCl, pH 7.4) for egg collection.

Laid eggs were collected and remaining unlaid eggs were expressed from the toads. Approximately 3000–5000 eggs were collected from each mature productive toad. The eggs were placed in deionized water for 5 minutes. The eggs were then dejellied in 2% freshly made cysteine (adjusted to pH 7.8 with NaOH) for 5 minutes at room temperature. The 2% cysteine solution was changed and the eggs were dejellied for another 5 minutes. The eggs were then washed three times in Barth solution (33 mM NaCl, 15 mM Tris HCl, 2 mM KCl, 1 mM $MgCl_2$, and 0.5 mM $CaCl_2$) using 10 ml/1000 eggs. The jelly coat of the eggs must be completely removed as judged by the lack of visible space between adjacent eggs. During the wash, eggs which appeared abnormal such as eggs that are exceptionally large were removed. In addition, eggs with necrotic changes or eggs that were discolored, lysed, or misshaped were removed.

The dejellied eggs were activated in 20 ml of Barth solution containing 0.5 µg/ml of the calcium ionophore A23187 (Sigma) for 2–5 minutes at room temperature. The ionophore A23187 can be stored at 1 µg/µl in dimethylsulfoxide (DMSO) at 4° C. Eggs that appeared to bind to the ionophore were removed. Successfully activated eggs (generally 95–100%) showed the pigments contracted to the animal pole. The eggs were rinsed three times with three volumes of ice-cold Extraction Buffer (50 mM KCl, 50 mM Hepes-KOH, 50 mM $MgCl_2$, and 2 mM β-mercaptoethanol). The eggs were then transferred to pre-chilled (4° C.) centrifuge tubes and packed to remove excess rinsing buffer by centrifuging at 1500 rpm for 1 minute in a pre-chilled SW50.1 rotor (Beckman) at 2° C.

A low-speed supernatant (LSS) of *Xenopus laevis* egg cytoplasm was prepared using a modification of the extraction procedure described previously (J. J. Blow and R. A. Laskey. Cell 47:577–587 (1986); J. J. Blow and P. Nurse. Cell 62:855–862 (1990)). The eggs were crushed by centrifugation at 10,000 rpm for 10 minutes in a SW50.1 rotor at 2° C. The egg components separated into three distinct layers. The three common fractions included: (1) a top layer of yellow yolk platelets and pigment, (2) a middle layer of golden cytoplasm, and (3) a bottom layer of cell debris containing membranes, organelles and DNA. The cytoplasmic layer was collected by puncturing the side of the centrifuge tube using a syringe with a 23 gauge needle. The cytoplasmic layer was supplemented with cytochalasin B (Sigma) in a 5 µg/µl DMSO stock solution and leupetin (Sigma) to achieve final concentrations of 10 µg/ml and 1 µg/ml respectively.

The cytoplasmic extracts were centrifuged again at 15,000 rpm for 10 minutes in a SW50.1 rotor at 2° C. to remove contaminants from the other fractions. The recentrifugation step separated the cytoplasm into a golden fraction above a loose yellow vesicular fraction. The golden fraction was collected and transferred to another tube. Care was taken to avoid contamination from the yellow vesicular fraction because that fraction has been found to be inhibitory to extract function. The egg extract was mixed with glycerol to a final concentration of 1% by volume. The egg extract was frozen and stored in liquid nitrogen in 50 µl aliquots.

Results

Figure 1A:
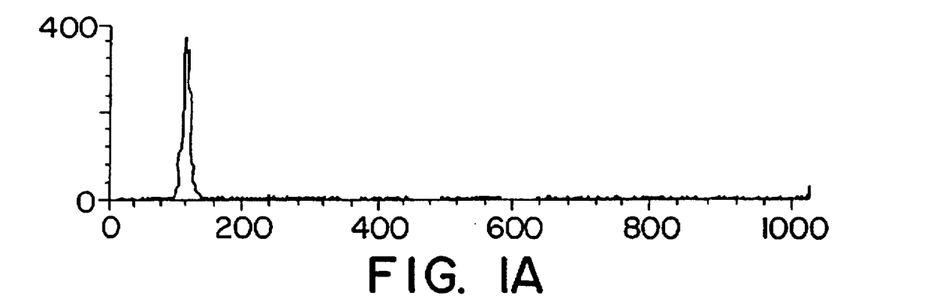
Figure 1B:
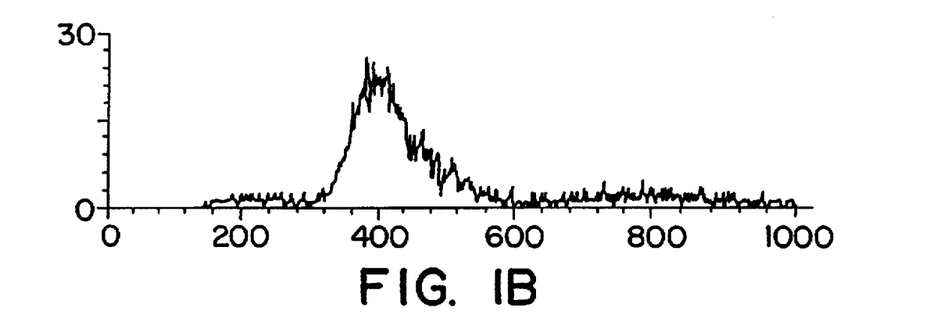
Figure 1C:
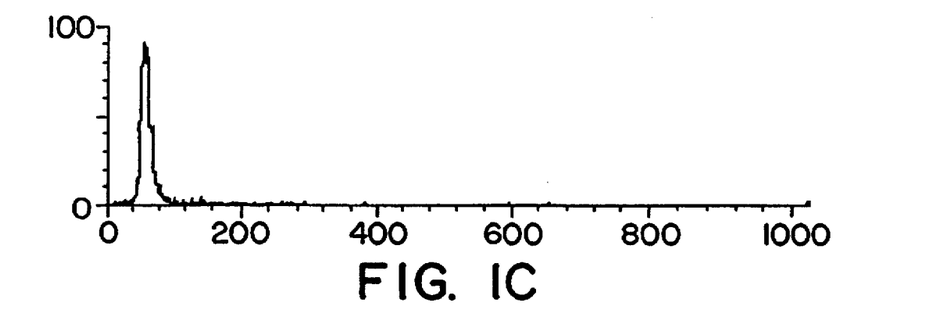
Figure 1D:
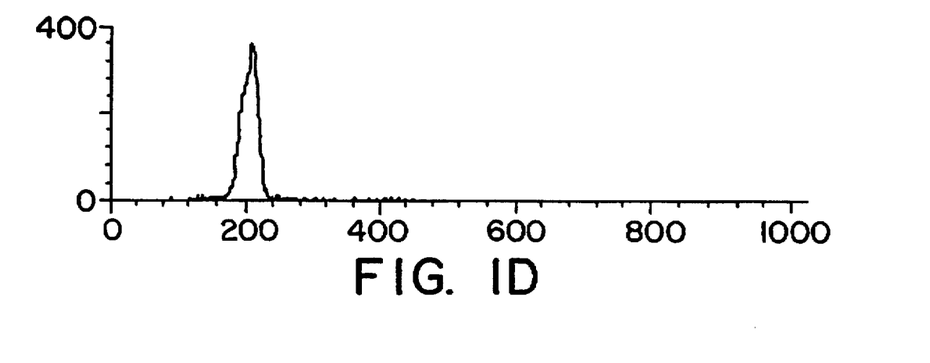
Figure 1E:
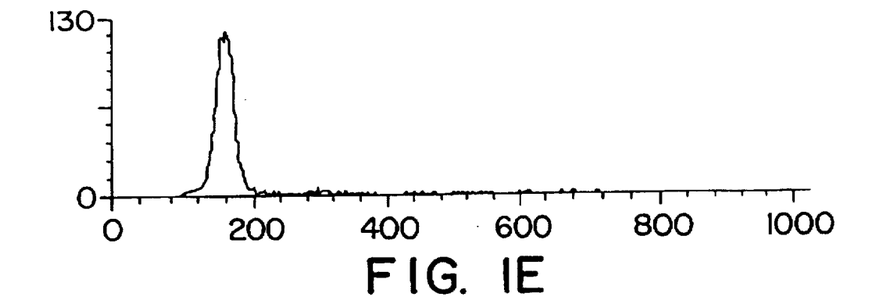

Xenopus laevis sperm were used to assess the quality of the Xenopus laevis egg extracts prepared using the protocol of the invention because Xenopus egg extracts have been well characterized with Xenopus sperm. Xenopus laevis sperm were prepared according to Murray (A. Murray, Meth. in Cell Biol. 36:581–605 (1991)). When Xenopus sperm nuclei were mixed with the Xenopus egg extract either with or without 100 µg/ml cycloheximide (CHM), the sperm nuclei rapidly decondensed and acquired a new nuclear membrane after 1.5 hours. The Xenopus sperm nuclei also began to undergo DNA synthesis. Decondensed Xenopus sperm were also incubated with the egg extract. The Xenopus sperm nuclei were decondensed in 3 mg/ml polyglutamic acid (MW 14,300, Sigma) for 40 minutes at room temperature. The fluorescence intensity of the decondensed Xenopus sperm was used as the haploid signal as described by Blow and Watson (J. J. Blow and J. V. Watson, *EMBO J.* 6:1997–2002 (1987)). The flow cytometric data in FIGS. 1A for decondensed Xenopus sperm and 1B for xenopus sperm show that after 4 hours, most of the Xenopus sperm nuclei were completely replicated. The rapidity of the decondensation and DNA synthesis events as well as the extent of DNA replication demonstrates that these egg extracts are highly active.

EXAMPLE 2

In Vitro Activation of Human Sperm Nuclei and Replication of Human Sperm Nuclei

Materials and Methods a. Preparation of Human Sperm Samples

Fresh or frozen semen samples were incubated at 37° C. for 30–60 minutes. The upper 200 µl of semen was then transferred to a 2-ml tube (USA/Scientific catalog #1420-2700) containing 1 ml of PBS (137 mM NaCl, 2.7 mM KCl, and 9.6 mM $Na_2HPO_4$, pH 7.4) and was mixed well. The semen was then filtered through a 15-µm mesh (Tetko, New York) and centrifuged at 2000 rpm in a GS-6 rotor (Beckman) in a swing bucket for 3 minutes to pellet the sperm. Sperm clumping has been a special problem for sperm purification. Usually, sperm are very "sticky" and they tend to clump together even at low centrifugation speeds. Clumping may be due to cell debris in the semen which causes the sperm to stick together. This problem can be overcome by filtering through a 15 µm mesh before centrifuging the sperm.

After centrifugation, the supernatant was discarded and the sperm were demembranated by adding 0.5 ml SuNaSp (250 mM sucrose, 75 mM NaCl, 0.5 mM spermidine, and 0.15 mM spermine) and 50 µl freshly made lysolecithin (LC) at a concentration of 10 mg/ml (Sigma catalog #L-4129) and incubating for 5 minutes at room temperature. Next, 1 ml of ice-cold SuNaSp containing 3% bovine serum albumin (BSA) (Sigma) was added to the demembranated sperm and the preparation was mixed well. The mixture was centrifuged at 2000 rpm in a GS-6 rotor for 5 minutes and the supernatant was discarded. The mixture was then washed twice with SuNaSp without BSA and 50 µl SuNaSp containing 30% glycerol was added. The preparation was mixed well, the sperm were counted and the preparation was stored at −80° C.

b. Replication Reaction

The first three steps of the replication reaction were completed during preparation of the egg extract if fresh egg extract was being used in the protocol. Two µl of demembranated sperm ($2 \times 10^4$/µl) were resuspended in 1 ml SuNASp, centrifuged at 2000 rpm in a GS-6 rotor for 5 minutes, and the supernatant was discarded. Next, 50–100 µl Extraction Buffer containing 5 mM dithiothreitol (DTT) were added and the mixture was incubated for 20–40 minutes at room temperature. The sperm were then washed again with SuNaSp solution by resuspending the sperm with 1 ml SuNaSp, centrifuging at 2000 rpm in a GS-6 rotor for 5 minutes and discarding the supernatant. The replication reaction was completed by adding 25 µl egg extract to the tube with $4 \times 10^4$ DTT-treated sperm for a concentration of 4–5 ng DNA or 1200–1500 sperm/µl extract. The replication reactions were supplemented with an ATP energy regeneration system with final concentrations of 1 mM ATP, 60 mM phosphocreatine and 150 µg/ml creatine phosphokinase. The four nucleotides dATP, dCTP, dGTP and dTTP were also included at concentrations of 50 µM per nucleotide. The samples were lightly shaken every 15 minutes to eliminate bubbles and to keep the reaction homogeneous. Addition of cycloheximide to the replication reaction at a final concentration of 100 µg/ml was optional.

DNA replication studies were also carried out on human sperm that were decondensed in vitro using heparin and β-mercaptoethanol instead of Xenopus laevis egg extract. These samples provided a control for comparison with the DNA replication results obtained when the human sperm were activated using the Xenopus egg extract.

To decondense the sperm, the sperm pellet was dissolved in SMT (250 mM sucrose, 5 mM $MgCl_2$, and 10 mM Tris HCl, pH 7.4) with a final sperm concentration of $2 \times 10^7$/ml. Two µl aliquots of sperm were frozen by plunging the tubes into liquid nitrogen and then thawing at room temperature. The freezing and thawing step was repeated twice. The sperm were then incubated in Decondensation Buffer (DB) (113 mM KCl, 12.15 mM $KH_2PO_4$, 2.5 mM $Na_2HPO_4$, 2.5 mM $MgCl_2$, 20 mM Tris, pH 7.4, 150 µm heparin, and 2 mM β-mercaptoethanol) at a concentration of $2 \times 10^6$ sperm/ml at 37° C. for 50–80 minutes. One µl aliquots of the sperm-DB mixture were removed and placed onto a slide with a drop of Fixation Buffer (FB) (SMT, 3.7% formalin, and 1 µg/ml propidium iodide or 10 µg/ml Hoechst 33342). Sperm nuclei decondensation was observed using an inverted phase-contrast microscope with a 40 × objective.

c. Bromodeoxyuridine Labeling

During bromodeoxyuridine (BrdU) incorporation analysis, light exposure was minimized throughout the procedure for all samples. To the appropriate replication reactions, BrdU was added to a final concentration of 40 µM. After incubating at room temperature for various time intervals ranging from 15 minutes to 9 hours, 1-µl aliquots were drawn from the replication reaction. Each aliquot was diluted with 1 µl PBS and transferred onto a poly-L-lysine-coated glass slide. After the aliquot became dry, sperm were fixed with ice-cold 70% ethanol for 15 minutes in the dark. The slide was next incubated in 4N HCl for 15 minutes at room temperature and then incubated with Anti-BrdU-FITC (Becton Dickinson, California). Following the antibody reaction with Anti-BrdU-FITC, the slide was stained with propidium iodide (PI) at a concentration of 0.04 µg/ml, washed with PBS, and mounted with an antifading mounting solution (100 mg/ml 1,4-diazo-bicyclo-octane in PBS mixed with an equal volume of glycerol, pH 8.6).

d. Flow Cytometry

For flow cytometric analysis, the replication reactions were stopped by diluting the reaction mixture in 0.5 ml of 10% sucrose in Buffer A (60 mM KCl, 15 mM Tris-HCl pH 7.4, 15 mM NaCl, 1 mM β-mercaptoethanol, 0.5 mM spermidine·3HCl, and 0.15 mM spermine·4HCl) and filtered through a 30-μm mesh (Tetko, NY). Before flow cytometric analysis, the pronuclei were stained by incubating for 1 hour at 4° C. after adding 25 μg PI and 0.35 U RNase. Flow cytometry was performed on an FACScan equipped with the LYSIS II software (Becton-Dickinson). Red-orange fluorescence (FL2) passing through a 585 nm bandpass filter was used to trigger signal processing and the area and width of the linearly amplified FL2 pulses were collected in a list mode for 5,000 to 10,000 events. For each sample, the data was gated to exclude debris. A gated histogram was then generated showing the amounts of fluorescence from the fluorescent-stained single nuclei.

Results a. In vitro Activation of Human Sperm Nuclei

One-μl aliquots were taken from a reaction of demembranated DTT-treated human sperm and Xenopus egg extract at separate time points. Morphological changes were analyzed by microscopic observation with a 40 × phase-optics lens (Nikon-Microphot-FXA). The most obvious morphological changes in the sperm heads occurred during the first 1–1.5 hours. The sperm heads treated with lysolecithin and DTT swelled relatively uniformly and by 30 minutes had reached diameters of 10–15 μm, which is a 40–130 fold increase in volume compared to the original size. Decondensation was followed by membrane structure formation as shown in FIGS. 1C through 1F. After decondensation, no obvious morphological changes were observed up to the 12 hour timepoint (See FIG. 1G).

b. DNA Replication of Human Sperm Genome

BrdU incorporation was used to qualitatively monitor replication of the human sperm DNA with the *Xenopus laevis* egg extracts. Human sperm DNA begin to replicate at 1.5 hours as indicated by BrdU incorporation. By 2.0 hours, the vast majority of sperm were shown to be BrdU positive. However, the labeling intensity was different among the sperm, indicating that human sperm nuclei assembled in Xenopus egg extracts initiate DNA synthesis asynchronously despite the common environment.

Flow cytometry was used to quantitatively monitor replication of the human sperm DNA with the *Xenopus laevis* egg extracts. The replication reactions were stopped at 1, 2, 4, 6, and 9 hours and samples were taken and analyzed with the flow cytometer FACScan (Becton-Dickinson) after PI staining. The fluorescence histograms from the sperm (or pronuclei) population are shown in FIGS. 1C–1L After 1 hour of incubation, the fluorescence peak of the sperm decondensed in the Xenopus egg extracts was centered at 158 which was lower than the peak observed at 207 for the decondensed with heparin and β-mercaptoethanol (See FIGS. 1D and 1E), but that peak was higher than the peak observed at 50–60 for sperm treated with only LC-DTT (See FIGS. 1C and 1E). The differences in fluorescence peaks observed for the sperm decondensed under varied conditions were presumably caused by the differences in chromosomal structures and accessibility for PI staining not in differences in DNA replication.

Figure 1F:
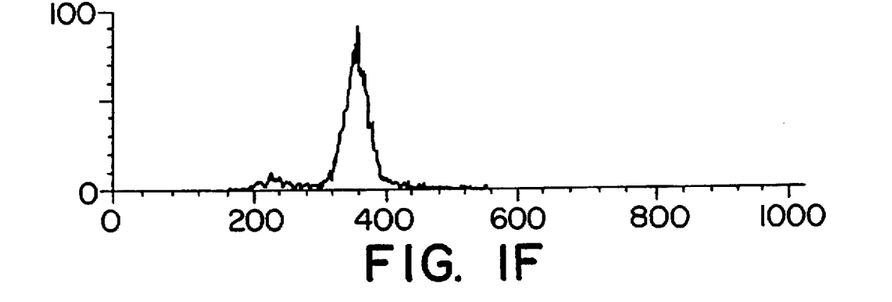
Figure 1G:
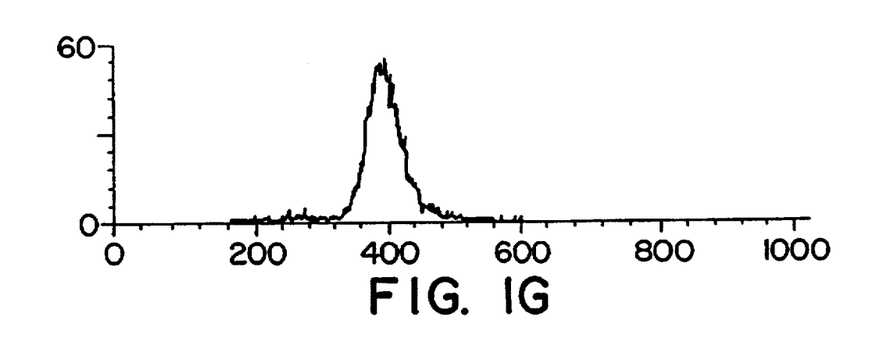
Figure 1H:
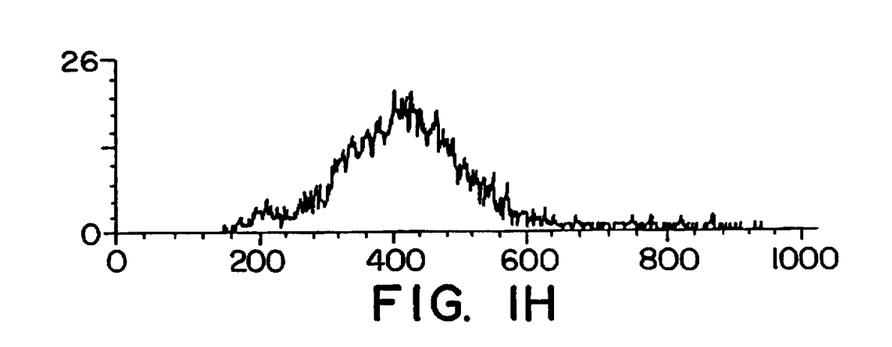
Figure 1I:
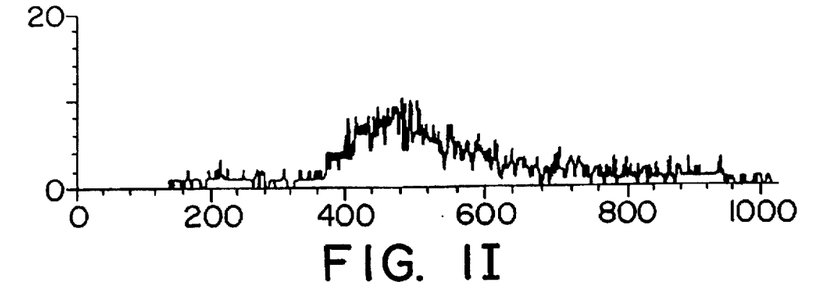
Figure 1J:
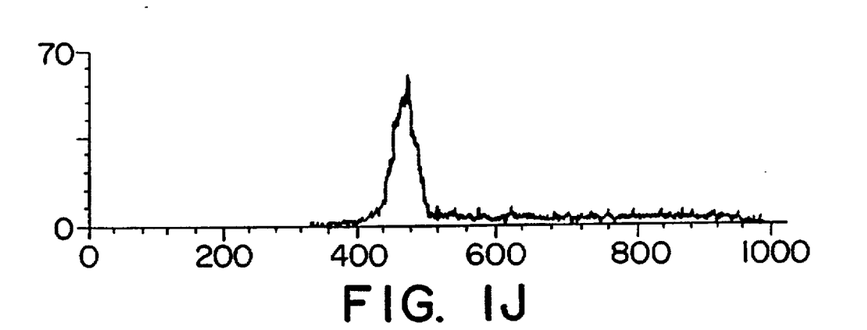

A major peak and minor peak were observed when the replication reaction was stopped at 2 hours (See FIG. 1F). The minor peak centered at 230 reflected the sperm with unreplicated genomes. The major peak centered at 357 should represent those with partially replicated genomes. As indicated, about 74% of the haploid genomes in about 85% of the sperm were replicated during the first 2 hours. At 4 hours, the peak from the replicated sperm (89%) was centered at 400 (See FIG. 1G). At 6 hours, the peak range became much broader from 257 to 604 (See FIG. 1H) and the peak range became even broader at 9 hours (See FIG. 1I). This change could be caused by pronuclei degradation and the resulting debris clumping caused by the nuclease released by the Xenopus egg extracts or by further replication after the completion of the first replication cycle. Although the peak continued to broaden, it was centered at 485 (See FIG. 1I) which was comparable to the peak centered at 472 observed for the normal human diploid cell line (See FIG. 1J). This indicates that the replication in a vast majority of the haploid human sperm could be completed. After 9 hours, the peak disappeared gradually, presumably because of the degradation of pronuclei.

In summary, the complete replication of the whole sperm genome could take up to 9 hours. DNA replication in human sperm was rapid in the first two hours when 74% of the haploid genomes were replicated (See FIG. 1F). After the two hour timepoint, replication became much slower.

Continuous DNA replication was confirmed by pulse labeling studies which showed continuous DNA replication in human sperm for 9 hours when it is incubated with Xenopus egg extracts. A 12.5 μl aliquot of Xenopus egg extract was incubated at room temperature with human sperm ($2\times10^4$ sperm heads in a volume of approximately 1 μl) for 6 hours. BrdU was then added to the reaction mixture to achieve a final concentration of 40 μM and the mixture was for 90 minutes. The reaction was terminated by the addition of 20 μl of PBS solution and the pronuclei were transferred to a glass slide. Microscopic observation showed some BrdU incorporation into pronuclei although it is less than the BrdU incorporation observed at 2 hours.

Similar results obtained when the replications reaction study was performed with or without cycloheximide (CHM). However, both microscopic and flow cytometric analyses indicated that after a 6 hour incubation period, more pronuclei remained intact when CHM was included in the replication reaction.

c. Effect of Factors on DNA Replication in Human Sperm

Figure 1K:
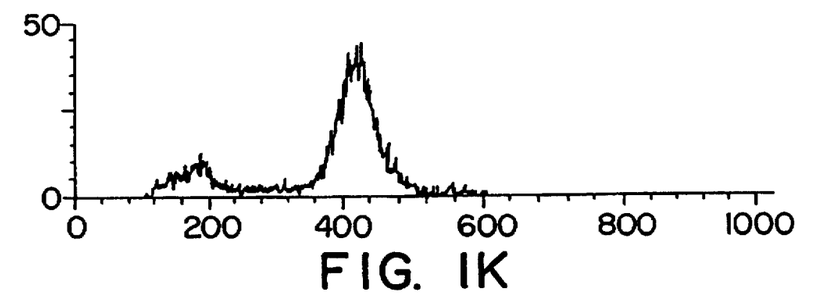
Figure 1L:
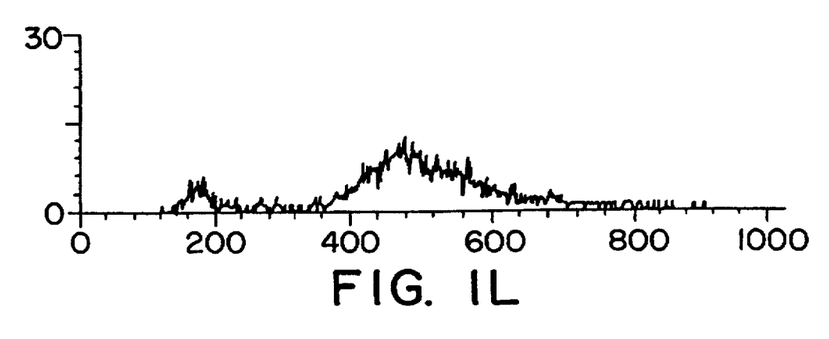

The speed and extent of DNA replication in human sperm varies considerably with *Xenopus laevis* egg extracts from different female toads. The extracts from some toads replicated the human sperm genome differently as shown in FIGS. 1K and 1L (Compare with FIGS. 1F and 1G, respectively). At 4 hours, about 12% of the sperm genomes remained unreplicated while 80% of the sperm had been completely replicated. Even after 6–12 hours, 5% of human sperm DNA remained unreplicated. These two populations displaying different degrees of replication can be distinguished by flow cytometric analysis. Microscopic observation showed that the sperm with unreplicated genomes are smaller than those with replicated genomes and furthermore, the sperm with unreplicated genomes have no clear surrounding membrane structure (data not shown) probably because those sperm did not completely decondense.

A very small portion of the unreplicated sperm DNA was sometimes observed even when the human sperm were incubated with the Xenopus egg extracts which were observed to support DNA replication in human sperm within 9 hours. This also occurred when Xenopus sperm was incubated with Xenopus egg extract (J. Blow, personal communication). In Xenopus sperm, this result is caused by incomplete demembranation by lysolecithin treatment of the Xenopus sperm and the failure of decondensation to occur.

Figure 1M:
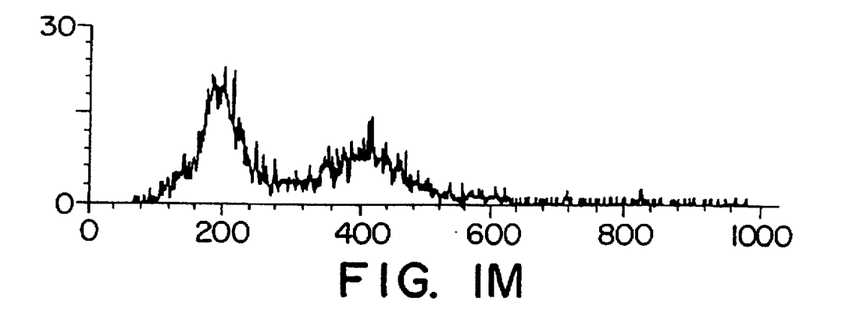
Figure 1N:
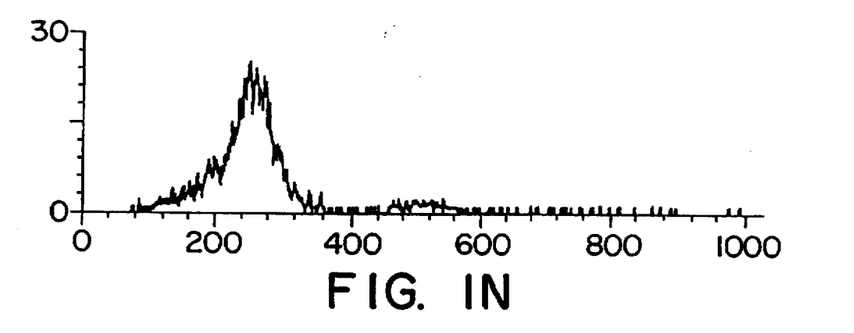

It has been shown that both activated and inactivated Xenopus egg extracts can support DNA replication in human sperm (J. J. Blow and R. A. Laskey, *Cell* 47:577–587 (1986); C. Smythe and J. W. Newport, *Meth. Cell Biol.* 35:449–467 (1991)). However, human sperm DNA replicates faster in the extracts from the eggs activated with calcium ionophore. Results from flow cytometric analysis in FIGS. 1M and 1N show that after 2 hours of incubation with extract from activated Xenopus eggs, 37% of the human sperm genomes started replication with the extract from activated Xenopus eggs. However, only 7% of the human sperm genomes started replication when incubated with extract from Xenopus eggs which had not been activated (See FIGS. 1M and 1N). The egg extract in both cases were collected from the same Xenopus toad.

Figure 1O:
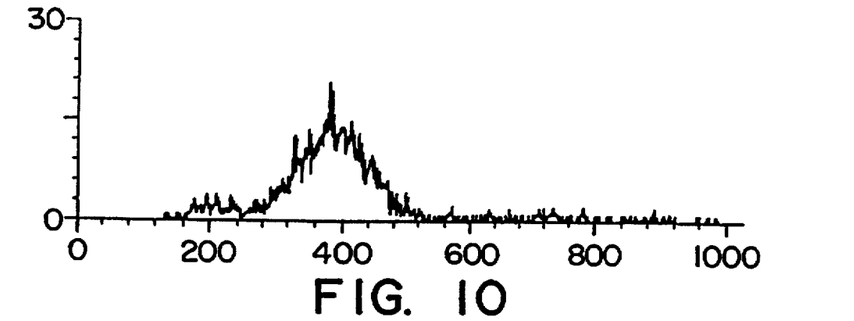
Figure 1P:
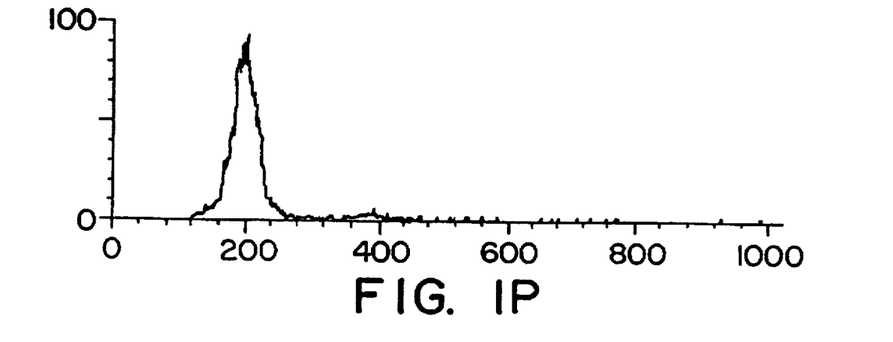

Frozen Xenopus egg extracts were used for the replication studies of both human and Xenopus sperm. Xenopus egg extract stored in liquid nitrogen for less than 1.5 months was as effective in supporting DNA replication in human sperm as fresh Xenopus egg extract (data not shown). However, after 1.5 months of frozen storage of Xenopus egg extract, the replication efficiency for human sperm DNA was significantly decreased. No obvious change was observed in the replication efficiency for xenopus sperm incubated with Xenopus egg extract that had been frozen for longer than 1.5 months (See FIGS. 1O and 1P).

The present invention is not limited to the particular embodiments described and exemplified, but is capable of variation and modification within the scope of the appended claims. For instance, cytoplasmic extracts from eggs of *Xenopus laevis* have been exemplified. However, it will be appreciated by those skilled in the art that egg extracts from other Xenopus species, or from other genera of frogs or toads, can be produced using the methods set forth within.

What is claimed is:

1. A composition comprising a purified cytoplasmic extract from eggs of *Xenopus laevis* which supports activation of human sperm and complete replication of a human sperm genome, said composition being prepared by a method comprising the steps of:
   a) providing a sexually mature female *Xenopus laevis* toad;
   b) priming said toad for egg production by administering to said toad a gonadotropin hormone in an amount effective to stimulate said egg production; said priming comprising:
      i) a first priming step wherein a first aliquot of pregnant mare gonadotropin is administered two days prior to egg collection; and
      ii) a second priming step wherein at least one additional aliquot of human chorionic gonadotropin is administered between about 12 and about 24 hours prior to egg collection;
   c) collecting the eggs;
   d) de-jellying the collected eggs;
   e) removing from the de-jellied eggs substantially all eggs which appear damaged or of non-uniform character as compared with normal, intact eggs from *Xenopus laevis*;
   f) activating the eggs to shift from mitotic phase to S phase in their cell cycle;
   g) rinsing the activated eggs with a compatible rinsing solution;
   h) packing the eggs by removing substantially all excess rinsing solution from the rinsed eggs;
   i) preparing an initial cytoplasmic fraction from the packed eggs by
      i) subjecting the eggs to centrifugation under conditions resulting in crushing of the eggs and separation of the initial cytoplasmic fraction from other egg components; and
      ii) collecting only the initial cytoplasmic fraction; and
   j) preparing the purified cytoplasmic extract from the initial cytoplasmic fraction by
      i) subjecting the initial cytoplasmic fraction to centrifugation under conditions resulting in separation of the purified cytoplasmic extract from vesicular components remaining in the initial cytoplasmic fraction;
      ii) collecting only said purified cytoplasmic extract; and
   k) optionally freezing and thawing said cytoplasmic extract, said extract retaining biological activity following said freezing and thawing.

2. The composition of claim 1, prepared by a method in which said removing from the de-jellied eggs substantially all damaged or non-uniform appearing eggs comprises manual removal of physically damaged eggs and eggs of non-uniform size, shape and color.

3. The composition of claim 2, prepared by a method in which said removing further comprises packing the eggs by centrifugation, decanting the rinsing solution from the packed eggs and skimming from the surface of the packed eggs said damaged or non-uniform appearing eggs, if present.

4. The composition of claim 1, prepared by a method in which said activation is accomplished by exposing the eggs to an amount of calcium ionophore effective to induce said shift from mitotic phase to S phase.

5. The composition of claim 1, prepared by a method in which said packing is accomplished by centrifugation and decanting of the rinsing solution from the packed eggs.

6. A method for completely replicating human sperm genomes, which comprises the steps of:
   a) providing the purified cytoplasmic extract of *Xenopus laevis* eggs as claimed in claim 1;
   b) providing a sample of demembranated, dithiothreitol-treated human sperm;
   c) initiating replication of genomes disposed within said human sperm by contacting said sperm with said egg extract in the presence of nucleotide triphosphates for DNA synthesis and reagents for regenerating ATP, said contacting producing a replication mixture; and
   d) continuing said replication for a time period sufficient to enable said complete replication of said human sperm genomes.

7. The method of claim 6, wherein said replication is quantitatively monitored at selected intervals during said time period.

8. The method of claim 7, wherein said quantitative monitoring is performed by a method comprising:
   a) removing an aliquot of the replication mixture;
   b) terminating the replication in the aliquot;
   c) uniformly labeling sperm nuclei in the aliquot with a quantitatable DNA-specific detectable reporter substance; and
   d) measuring the quantity of the detectable reporter substance in the aliquot, said quantity being directly proportional to the amount of DNA in each sperm nucleus present in the aliquot.

9. The method of claim 8, wherein said measuring is performed by flow cytometry.

10. The method of claim 9, wherein the detectable reporter substance is propidium iodide.

11. The method of claim 6, wherein the *Xenopus laevis* egg cytoplasmic extract has been frozen and thawed.

12. A method of preparing a purified cytoplasmic extract from eggs of *Xenopus laevis* which supports activation of human sperm and complete replication of a human sperm genome, said method comprising the steps of:
   a) providing a sexually mature female *Xenopus laevis* toad;
   b) priming said toad for egg production by administering to said toad a gonadotropin hormone in an amount effective to stimulate said egg production; said priming comprising:
      i) a first priming step wherein a first aliquot of pregnant mare gonadotropin is administered two days prior to egg collection; and
      ii) a second priming step wherein at least one additional aliquot of human chorionic gonadotropin is administered between about 12 and about 24 hours prior to egg collection;
   c) collecting the eggs;
   d) de-jellying the collected eggs;
   e) removing from the de-jellied eggs substantially all eggs which appear damaged or of non-uniform character as compared with normal, intact eggs from *Xenopus laevis*;
   f) activating the eggs to shift from mitotic phase to S phase in their cell cycle;
   g) rinsing the activated eggs with a compatible rinsing solution;
   h) packing the eggs by removing substantially all excess rinsing solution from the rinsed eggs;
   i) preparing an initial cytoplasmic fraction from the packed eggs by
      i) subjecting the eggs to centrifugation under conditions resulting in crushing of the eggs and separation of the initial cytoplasmic fraction from other egg components; and
      ii) collecting only the initial cytoplasmic fraction; and
   j) preparing the purified cytoplasmic extract from the initial cytoplasmic fraction by
      i) subjecting the initial cytoplasmic fraction to centrifugation under conditions resulting in separation of the purified cytoplasmic extract from vesicular components remaining in the initial cytoplasmic fraction;
      ii) collecting only said purified cytoplasmic extract; and
   k) optionally freezing and thawing said extract said extract maintaining biological activity following said freezing and thawing.

13. The method of claim 12, in which said activation is accomplished by exposing the eggs to an amount of calcium ionophore effective to induce said shift from mitotic phase to S phase.

14. The method of claim 12, wherein said freezing is accomplished by immersing the extract in liquid nitrogen.

15. The method of claim 12, in which said packing is accomplished by centrifugation and decanting of the rinsing solution from the packed eggs.

16. The method of claim 12, in which said removing from the de-jellied eggs substantially all damaged or non-uniform appearing eggs comprises manual removal of physically damaged eggs and eggs of non-uniform size, shape and color.

17. The method of claim 16, in which said removing further comprises packing the eggs by centrifugation, decanting the rinsing solution from the packed eggs and skimming from the surface of the packed eggs said damaged or non-uniform appearing eggs, if present.

18. A method for quantitative assessment of DNA replication in a test sample of human sperm from a suspected infertile donor, which comprises:
   a) providing the purified cytoplasmic extract of *Xenopus laevis* eggs as claimed in claim 1, said extract being supplemented with nucleotide triphosphates for DNA synthesis and reagents for regenerating ATP, thereby producing a replication solution;
   b) providing a test sample of demembranated, dithiothreitol-treated sperm from said suspected infertile donor;
   c) providing a control sample of demembranated, dithiothreitol-treated sperm from a known fertile donor;
   d) initiating a test replication reaction by combining said test sample sperm with said replication solution;
   e) initiating a control replication reaction by combining said control sample sperm with said replication solution;
   f) continuing said control replication reaction and said test replication reaction for a predetermined time period;
   g) at selected intervals during said time period, removing equivalent aliquots of each of the control and test replication reactions;
   h) terminating the replication in each said aliquot;
   i) uniformly labeling sperm pronuclei from each said aliquot with a quantitatable DNA-specific detectable reporter substance;
   j) measuring the quantity of the detectable reporter substance in each said aliquot, said quantity being directly proportional to the amount of DNA in each nucleus present in each said test replication reaction and said control replication reaction at said selected interval; and
   k) comparing the amount of DNA present in the test replication reaction with the amount of DNA present in the control replication reaction at said selected interval.

19. The method of claim 18, wherein said cytoplasmic egg extract is frozen and thawed prior to being provided.

20. The method of claim 18, wherein said measuring is performed by flow cytometry.

21. The method of claim 20, wherein said detectable reporter substance is propidium iodide.

* * * * *